United States Patent
Lashinski

(10) Patent No.: US 9,610,156 B2
(45) Date of Patent: Apr. 4, 2017

(54) MITRAL VALVE INVERSION PROSTHESES

(71) Applicant: MILLIPEDE, INC., Santa Rosa, CA (US)

(72) Inventor: Randall Lashinski, Windsor, CA (US)

(73) Assignee: Millipede, Inc., Santa Rosa, CA (US)

( * ) Notice: Subject to any disclaimer, the term of this patent is extended or adjusted under 35 U.S.C. 154(b) by 0 days.

(21) Appl. No.: 14/427,909

(22) PCT Filed: Sep. 13, 2013

(86) PCT No.: PCT/US2013/059751
§ 371 (c)(1),
(2) Date: Mar. 12, 2015

(87) PCT Pub. No.: WO2014/043527
PCT Pub. Date: Mar. 20, 2014

(65) Prior Publication Data
US 2015/0238312 A1     Aug. 27, 2015

Related U.S. Application Data

(60) Provisional application No. 61/700,989, filed on Sep. 14, 2012.

(51) Int. Cl.
*A61F 2/24*     (2006.01)
*A61H 23/00*    (2006.01)

(52) U.S. Cl.
CPC .......... *A61F 2/2409* (2013.01); *A61F 2/2436* (2013.01); *A61F 2/2442* (2013.01);
(Continued)

(58) Field of Classification Search
CPC ........ A61F 2/24; A61F 2/2409; A61F 2/2487; A61F 2/2466; A61F 2/848;
(Continued)

(56) References Cited

U.S. PATENT DOCUMENTS 3,143,742 A    8/1964  Cromie
7,655,040 B2 * 2/2010  Douk ............... A61B 17/00234
                                                 606/151

(Continued)

FOREIGN PATENT DOCUMENTS

WO    WO 2010/011699        1/2010
WO    WO 2010/011699 A2     1/2010

OTHER PUBLICATIONS

International Search Report for PCT/US2013/059751 dated Dec. 11, 2013.

(Continued)

*Primary Examiner* — David Isabella
*Assistant Examiner* — Dinah Baria
(74) *Attorney, Agent, or Firm* — Knobbe, Martens, Olson & Bear, LLP

(57) ABSTRACT

Systems, devices and methods for heart valve prostheses are described. An implant is inserted proximate a mitral valve, and has a tubular body and a plurality of piercing members, the tubular body comprising an upper diameter and a lower diameter. Tissue proximate the mitral valve is engaged by the plurality of piercing members and the tubular body transitions from a first structural configuration to a second structural configuration by application of an expansive force to the tubular body proximate the upper diameter, the first structural configuration having the upper diameter smaller than the lower diameter and the second structural configuration having the upper diameter larger than the lower diameter.

7 Claims, 14 Drawing Sheets

(52) U.S. Cl.
CPC .......... *A61F 2/2445* (2013.01); *A61H 23/00* (2013.01); *A61F 2/24* (2013.01); *A61F 2/2457* (2013.01); *A61F 2/2466* (2013.01); *A61F 2/2487* (2013.01); *A61F 2220/0016* (2013.01); *A61F 2250/001* (2013.01)

(58) Field of Classification Search
CPC ........ A61F 2250/001; A61F 2220/0016; A61F 2002/8483; A61F 2/2442; A61F 2/2445; A61F 2/2427; A61F 2/2454; A61H 23/00
See application file for complete search history.

(56) References Cited

U.S. PATENT DOCUMENTS

| | | |
|---|---|---|
| 2004/0049266 A1 | 3/2004 | Anduiza et al. |
| 2004/0260394 A1 | 12/2004 | Douk et al. |
| 2009/0276040 A1 | 11/2009 | Rowe et al. |
| 2010/0004740 A1 | 1/2010 | Seguin et al. |
| 2011/0172760 A1* | 7/2011 | Anderson .......... A61B 17/0057 623/1.15 |
| 2012/0022640 A1 | 1/2012 | Gross et al. |
| 2012/0053680 A1 | 3/2012 | Bolling et al. |

OTHER PUBLICATIONS

Extended European Search report in European Application No. EP 13837432.7, dated Jun. 13, 2016.
Extended European Search Report dated Jun. 13, 2016 in European patent application No. 13837432.7.

* cited by examiner

MITRAL VALVE INVERSION PROSTHESES

CROSS REFERENCE TO RELATED APPLICATIONS

This application is a U.S. National Phase Application of PCT International Application Number PCT/US2013/059751, filed on Sep. 13, 2013, designating the United States of America and published in the English language, which is an International Application of and claims the benefit of priority to U.S. Provisional Application No. 61/700,989, filed on Sep. 14, 2012. The disclosures of the above-referenced applications are hereby expressly incorporated by reference in their entireties. Any and all priority claims identified in the Application Data Sheet, or any correction thereto, are hereby incorporated by reference under 37 C.F.R. §1.57.

TECHNICAL FIELD OF THE DISCLOSURE

This disclosure relates generally to cardiac treatment devices and techniques, and in particular, to methods and devices for repair of mitral valve defects such as mitral valve regurgitation.

BACKGROUND

The mitral valve is one of four heart valves that direct blood through the two sides of the heart. The mitral valve itself consists of two leaflets, an anterior leaflet and a posterior leaflet, each of which are passive in that the leaflets open and close in response to pressure placed on the leaflets by the pumping of the heart.

Among the problems that can develop or occur with respect to the mitral valve is mitral valve regurgitation (MR), in which the mitral valve leaflets become unable to close properly, thus causing leakage of the mitral valve. Severe mitral regurgitation is a serious problem that, if left untreated, can adversely affect cardiac function and thus compromise a patient's quality of life and life span.

Currently, mitral regurgitation is diagnosed by many indicators, and the mechanism of mitral regurgitation can be accurately visualized by trans-esophageal echocardiography or fluoroscopy with dye injection. The most prevalent and widely accepted current technique to correct mitral regurgitation is to repair the mitral valve via open-heart surgery while a patient's heart is stopped and the patient is on cardiopulmonary bypass, a highly invasive procedure that has inherent risks.

SUMMARY

In one embodiment, the present disclosure includes a method comprising inserting an implant proximate a mitral valve, the implant comprising a tubular body and a plurality of piercing members, the tubular body comprising an upper diameter and a lower diameter. The method also includes engaging tissue proximate the mitral valve by the plurality of piercing members and transitioning the tubular body from a first structural configuration to a second structural configuration by application of an expansive force to the tubular body proximate the upper diameter, the first structural configuration having the upper diameter smaller than the lower diameter and the second structural configuration having the upper diameter larger than the lower diameter.

In an alternative embodiment, the present disclosure includes an implant comprising a tubular body comprising an upper diameter and a lower diameter, the tubular body having a first structural configuration in which the upper diameter is smaller than the lower diameter and a second structural configuration in which the upper diameter is larger than the lower diameter, the tubular body configured to transition from the first structural configuration to the second structural configuration by application of an expansive force to the tubular body proximate the upper diameter. The implant also comprises a plurality of piercing members connected to the tubular body and proximate the lower diameter to engage tissue proximate a mitral valve.

In an additional embodiment, the present disclosure includes a system comprising a guide wire, a sheath over the guide wire, and an implant for delivery to a body by traveling through the sheath and along the guide wire. The implant comprises a tubular body comprising an upper diameter and a lower diameter, the tubular body having a first structural configuration in which the upper diameter is smaller than the lower diameter and a second structural configuration in which the upper diameter is larger than the lower diameter, the tubular body configured to transition from the first structural configuration to the second structural configuration by application of an expansive force to the tubular body proximate the upper diameter. The implant also comprises a plurality of barbs connected to the tubular body and proximate the lower diameter to penetrate tissue proximate a mitral valve.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

The present disclosure relates to an implant including a tubular body and piercing members for reshaping a mitral valve suffering from mitral regurgitation. The implant may include two or more structural configurations. In a first structural configuration, an upper diameter (away from the mitral valve) may be smaller than a lower diameter (proximate the mitral valve). In this first structural configuration, the piercing members of the implant may engage the tissue proximate the mitral valve, for example, the mitral valve annulus. The implant may then be transitioned from the first structural configuration to a second structural configuration in which the size of the upper diameter is larger than the lower diameter. This may be facilitated by an expansive force causing the upper diameter to expand, in turn causing the lower diameter to contract. As the lower diameter contracts, the penetrating members engaged with the tissue proximate the mitral valve may cause the mitral valve to also contract to a smaller diameter. This may allow the valve leaflets to close properly, addressing mitral regurgitation.

Figure 1A:
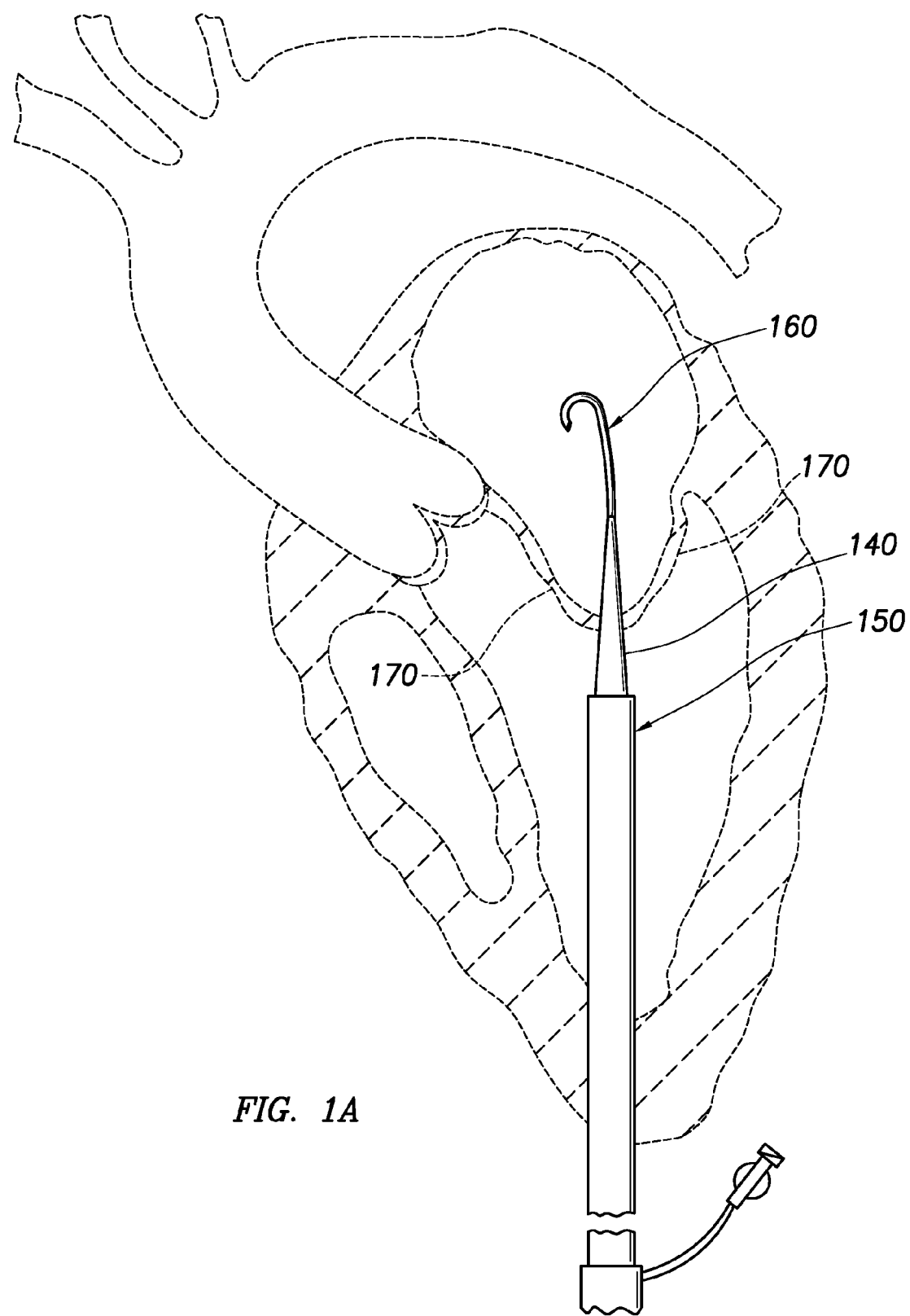
FIGS. 1A-1F illustrate an example embodiment of an implant in accordance with the present disclosure.

FIGS. 1A-F illustrate one embodiment of an implant. For example, as shown in FIG. 1A, in some embodiments, repair of a mitral valve may be achieved by a catheter system and catheterization procedure, wherein a catheter may be configured for percutaneous access to the mitral valve through the left ventricle. Access may be granted to the left ventricle through the apex of the heart where an incision may be made to insert a dilator and sheath 150 for access of a repair catheter 140. Sheath 150 may measure about six French to about thirty French and a closure device may be used in conjunction with the entry of this access catheter 140.

In one embodiment of the present disclosure, catheter 140 may include an extendable guide wire assembly 160, which may guide the system into position. Guide wire 160 may measure between 0.010 inches and 0.038 inches in diameter, and may be 0.035 inches in diameter. Catheter 140 or sheath 150 when accessed through the apex of the heart may measure about twenty to thirty centimeters in length.

Figure 1B:
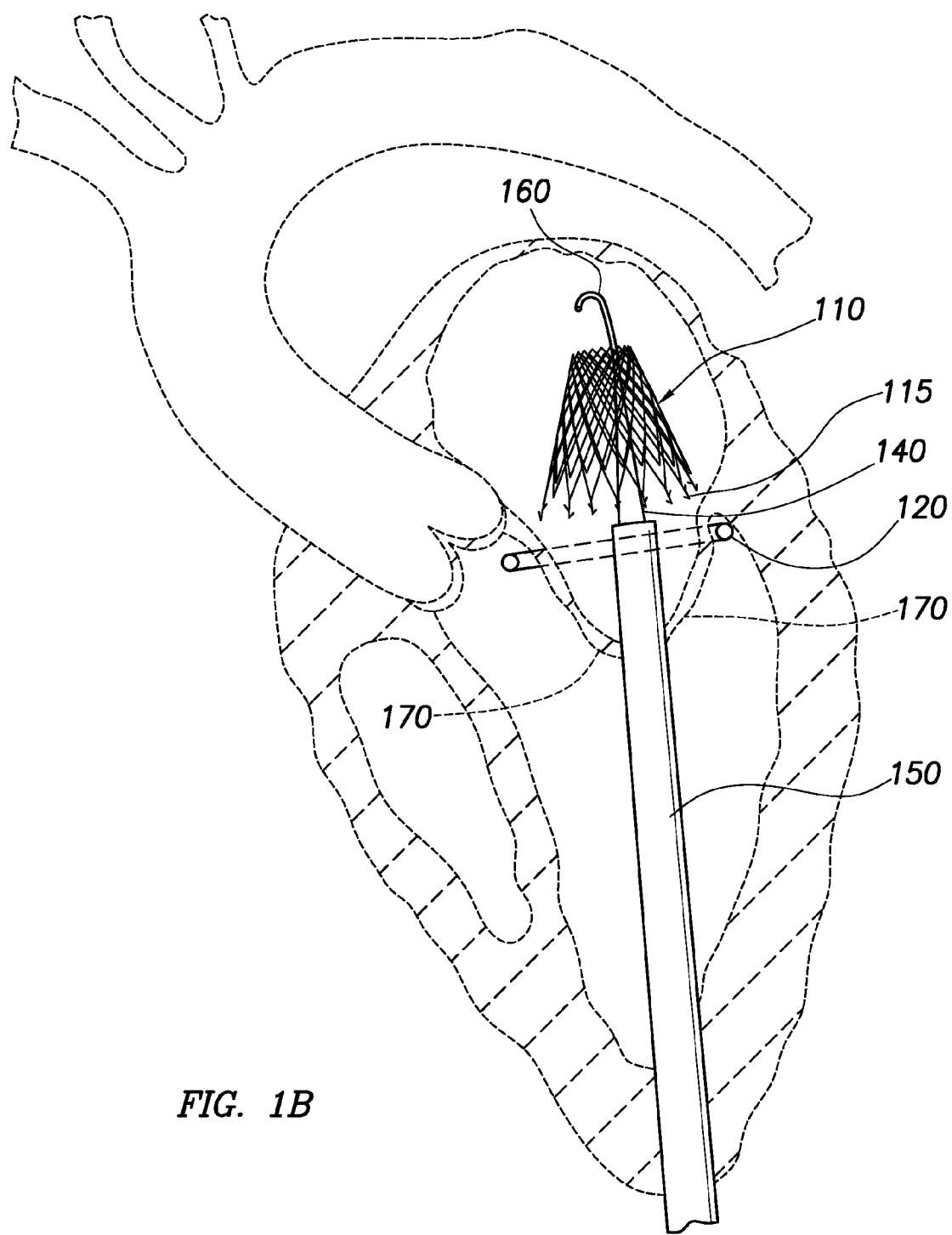

As shown in FIG. 1B, once access has been achieved, a delivery system may be introduced through sheath 150 along guide wire 160 with implant 110 for reducing the diameter of the mitral valve annulus. Catheter 140 may deliver implant 110 to resize the mitral valve to reduce the mitral valve cross sectional area or move the posterior leaflet back into position limiting or reducing mitral valve regurgitation.

Implant 110 may include a tubular body with portions of the tube removed similar to a stent structure where a portion of the material may be removed via laser cutting or other means to selectively cut portions of the tube away forming a radially-expandable tubular body. Implant 110 may be introduced in a collapsed structural configuration. This collapsed structural configuration may allow implant 110 to fit within sheath 150 to allow for a percutaneous procedure rather than an open-heart procedure. As shown in FIG. 1B, once implant 110 arrives in the left atrium, implant 110 may be expanded to a larger first structural configuration to engage tissue proximate the mitral valve, for example, the mitral valve annulus. In one embodiment, implant 110 may have a tubular shape with a free diameter of about twenty five to about thirty five millimeters in diameter, a height of about ten to about thirty millimeters, and a wall thickness of between about 0.005 inches and about 0.040 inches. Implant 110 may be constructed of a metallic material such as stainless steel, MP35N alloy, Nitinol or other implantable material.

In some embodiments, implant 110 may be tapered such that one end may be larger in diameter than the other end, appearing generally frustoconical in shape. The diameters of the ends may be approximately twenty five millimeters on the smaller end and approximately thirty five millimeters on the larger end. Implant 110 may also be non-circular where a portion of the implant may be elliptical or include a radial portion that is flat. This flat portion may be oriented toward the aortic valve and the circular portion may be positioned toward the posterior leaflet. To facilitate discussion of implant 110, an upper portion and lower portion may be described. The lower portion may refer to the end of implant 110 proximate mitral valve 170 while the upper portion may refer to the end of implant 110 free in the left atrium.

Implant 110 may include piercing members 115 proximate the lower portion of implant 110 proximate mitral valve 170 to engage with tissue proximate mitral valve 170, for example, the mitral valve annulus. Piercing members 115 may include barbs or hooks similar to fish hook barbs or other similar feature to resist withdrawal from tissue once pierced. Piercing members 115, barbs or hooks of the piercing members 115, or any combination thereof may pierce the tissue to engage with the tissue. Piercing members 115 may include a singular barb or hook, or a plurality of barbs or hooks per piercing member 115. Piercing members 115 may be immediately exposed or covered for delivery. They may number from one to fifty and may have a length of about four to twenty millimeters in length. They may have the same wall thickness as a wall of the tubular body of implant 110 or may differ with an increased or decreased thickness or taper in either direction to allow for mechanical integrity.

Piercing members 115 of implant 110 may be integral or attached to implant 110 as a secondary component glued, welded, or attached as an ancillary part. Piercing members 115 may also be laser cut into implant 110, and therefore attached to implant 110. The barbs or hooks may be fatigue resistant from fracture or separation from piercing members 115. For example, the barbs or hooks may have additional strength or wall thickness at the connection to piercing members 115. The barbs or hooks may also be attached with a hinged attachment allowing motion relative to the heart, but not longitudinally where the barbs or hooks may separate from piercing member 115.

The barbs or hooks of piercing member 115 may be active or passive meaning that the barbs or hooks may be activated with heat to bend or expose or mechanically formed through an external force to bend or expose. For example, each barb or hook may be sheathed inside a tube and removal of this tube may allow the barb or hook to be activated by, for example, body heat or some other activation factor, such that the barb or hook is exposed so as to engage the surrounding tissue. In a passive configuration, the barbs or hooks may be static in nature and either always exposed or exposed as soon as a covering is removed. The barbs or hooks may be hidden until deployment limiting the exposure during delivery and positioning and only exposed once positioning is finalized. The exposure may be completed as individual barbs or as multiples of barbs. In some embodiments, the covering is thus only a temporary covering.

As shown in FIG. 1B, in some embodiments, implant 110 may be positioned at the annulus of mitral valve 170 where the mitral valve hinge meets the left ventricle and the left atrium meets mitral valve 170. Positioning implant 110 at this location may be facilitated using a location ring 120. For example, location ring 120 may be positioned within the left ventricle, under mitral valve 170. A catheter to deliver location ring 120 may be placed in the left ventricle via the same access point through sheath 150. In some embodiments, location ring 120 may comprise a metallic ring or coiled section, which may be viewed via fluoroscopy or echo guidance to confirm the location of location ring 120. This may allow confirmation of a positive location for implant 110 to be located with respect to the mitral valve annulus. In addition to the use of a location ring, other methods for determining a desired location to attach implant 110 may could include echo guidance, CT, fluoroscopy or MRI other imaging techniques to highlight the mitral valve hinge.

Figure 1C:
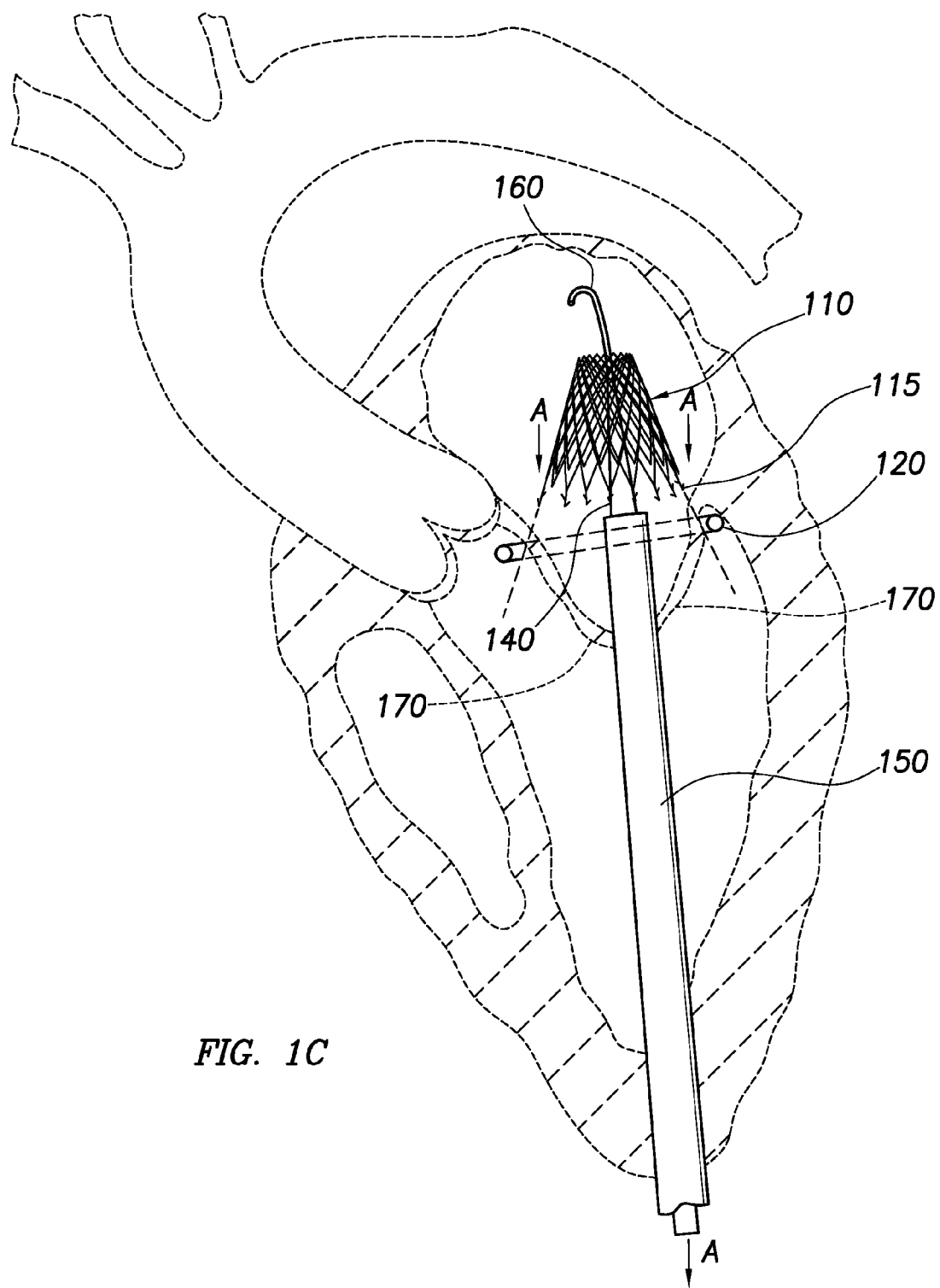

As shown in FIG. 1C, while in a first expanded structural configuration, and once a proper position has been achieved, implant 110 may have a downward force "A" applied to cause piercing members 115 to engage with and/or pierce the mitral valve annulus. This force may be applied by the delivery system itself, or may be applied by a secondary catheter that may be introduced for engaging piercing members 115 with the tissue proximate mitral valve 170.

Figure 1D:
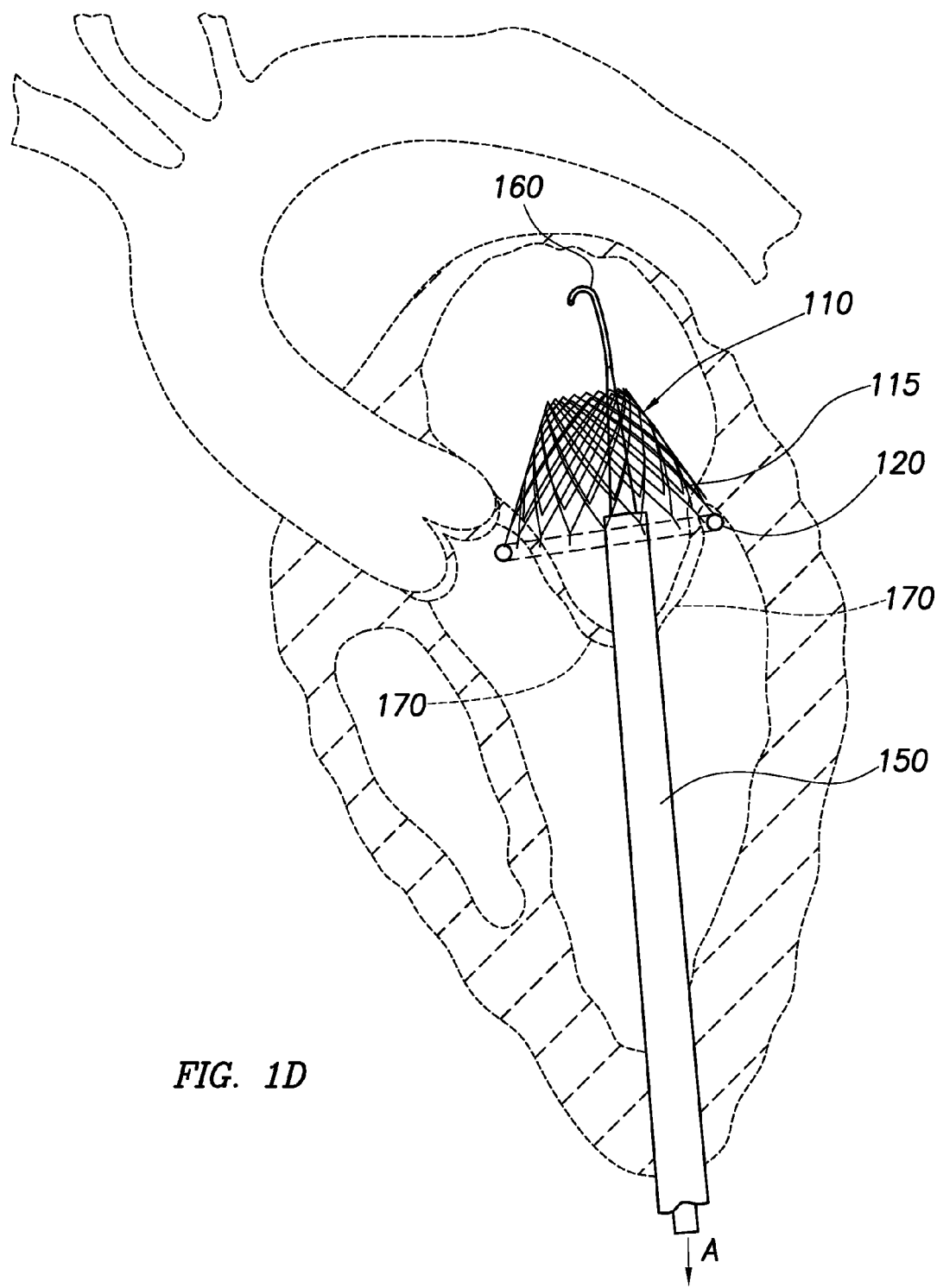

As shown in FIG. 1D, in some embodiments, location ring 120 may also act as an anchor for implant 110. In such an embodiment, implant 110 above mitral valve 170 (i.e. in the left atrium side of mitral valve 170) may attach to location ring 120 below mitral valve 170 (i.e. in the left ventricle side of mitral valve 170). For example, the hooks or barbs of piercing members 115 may engage with location ring 120. This may be accomplished by a through suture, a barbed means, wrapping or clipping location ring 120 to implant 110. Magnetic forces may also hold location ring 120 and implant 110 together either temporarily or permanently. Alternatively, the hooks or barbs may also be attached to some other separate implant below mitral valve 170 in the left ventricle. This may be a wire, ring, or tee anchor to secure implant 110 to via wires, threads or mechanical means to attach through the tissue median. For convenience, this implant below mitral valve 170 may be referred to as location ring 120, even if not used in locating implant 110 proximate mitral valve 170.

In some embodiments, the shape of location ring 120 may be a circular cross section measuring about 0.010 inches to about 0.090 inches in diameter and may encircle the mitral annulus. The shape may also be non-circular, oval, biased to one axis or multi-axis to accommodate the multi-plane shape of mitral valve 170, which is more saddle shaped. It may also have a variable stiffness in different sections to accommodate tighter bends in the placement of location ring 120. Location ring 120 and or a delivery catheter may also be steerable to navigate the area under mitral valve 170 for ease of placement. Utilizing push pull wires to compress or load portions of the catheter or location ring 120 to predictably bend and orient the catheter or location ring 120 may allow a user to access difficult anatomical features en route to and around mitral valve 170.

Figure 1E:
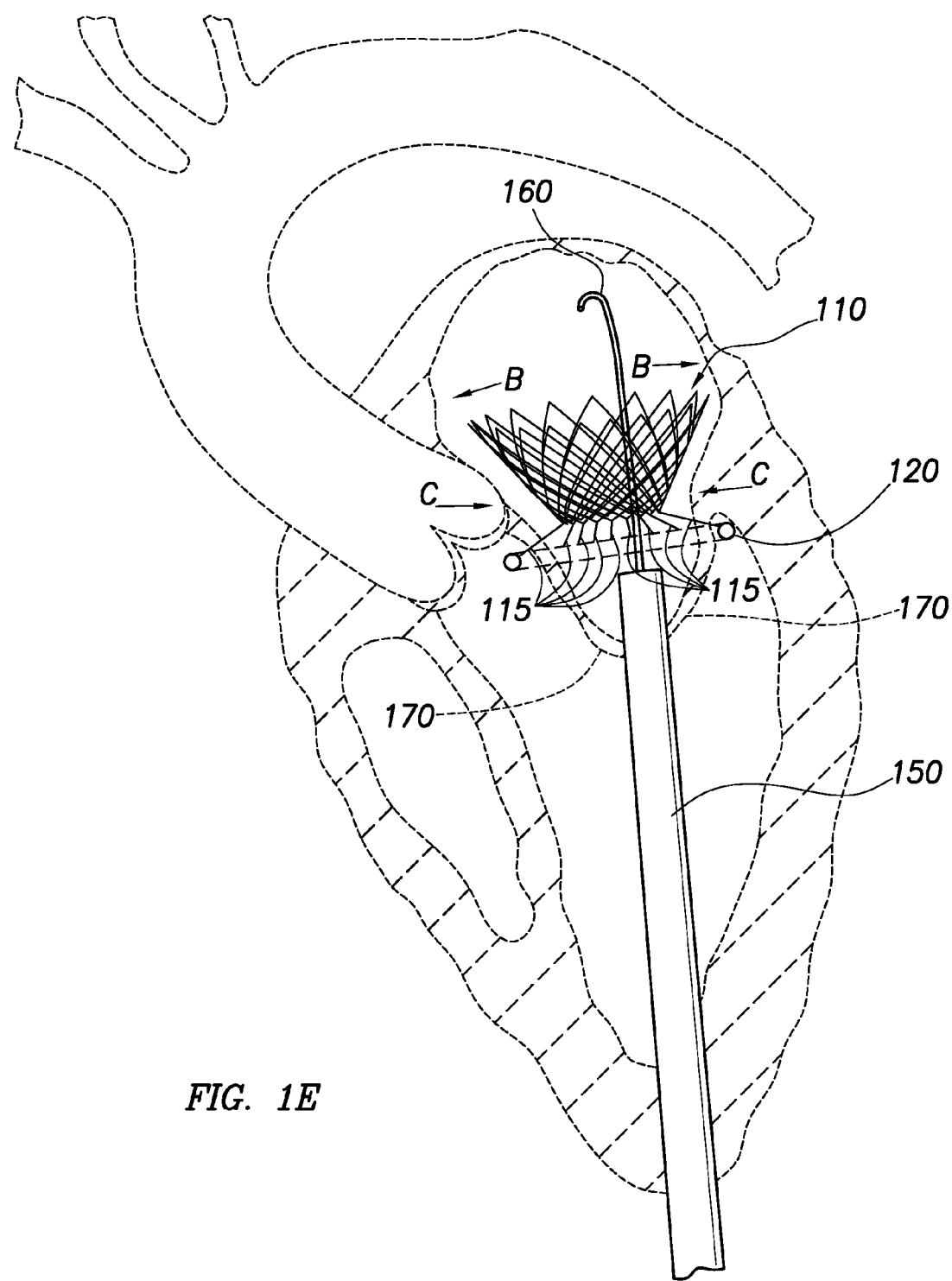

As shown in FIG. 1E, once piercing members 115 have engaged the tissue proximate mitral valve 170, for example, the mitral valve annulus, an expansive force "B" may be applied to the upper portion of implant 110. By applying expansive force "B" to implant 110, a reactive reducing force "C" may also be produced at the lower portion of implant 110. As the diameter of the lower portion is decreased from reactive reducing force "C," the diameter of mitral valve 170 is also reduced due to the attachment of implant 110 to the tissue around mitral valve 170. For example, once a sufficient reducing force "C" has been generated to reshape mitral valve 170 to a desired size, implant 110 may be left in a final position in which the size change of mitral valve 170 may be maintained. This may be a second structural configuration.

Figure 1F:
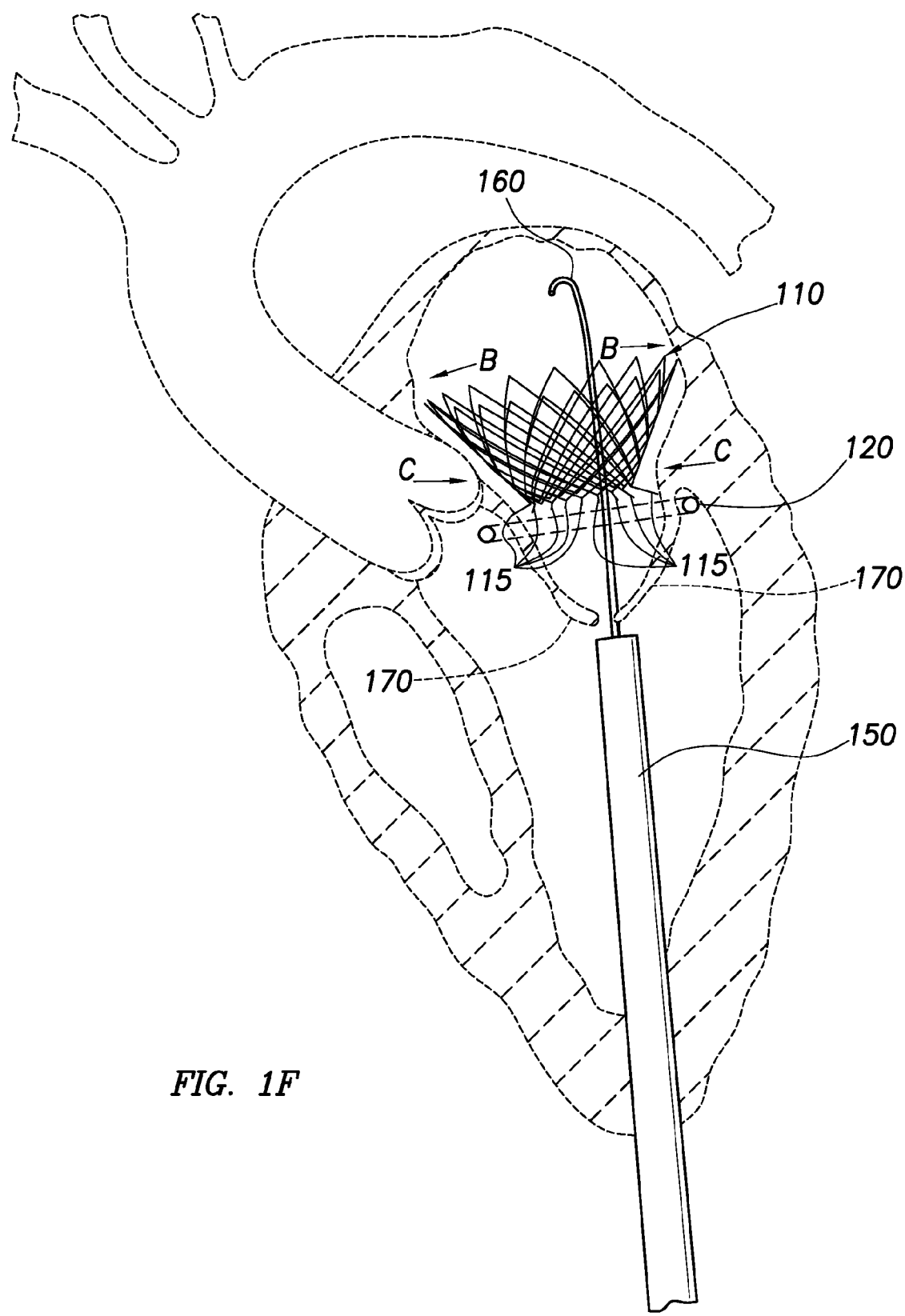

As shown in FIG. 1F, in some embodiments, piercing members 115 may engage the tissue proximate mitral valve 170 but not engage location ring 120. In such an embodiment, the barbs or hooks of piercing members 115 may bind, engage with, and/or resist withdrawal from tissue proximate mitral valve 170 in a manner sufficient to keep implant 110 attached to the tissue proximate mitral valve 170. Additionally, the binding, engaging, and/or resisting withdrawal may be sufficient to decrease the surface area of mitral valve 170 as expansive force "B" and reactive reducing force "C" are applied. In such an embodiment, location ring 120 may or may not be used to facilitate placing implant 110 at a positive location proximate mitral valve 170. A positive location for implant 110 may be one in which implant 110 is able to engage tissue proximate mitral valve 170 without impairing the function of mitral valve 170 and further implant 110 may be used to decrease the surface area of mitral valve 170 as expansive force "B" and reactive reducing force "C" are applied.

Figure 2A:
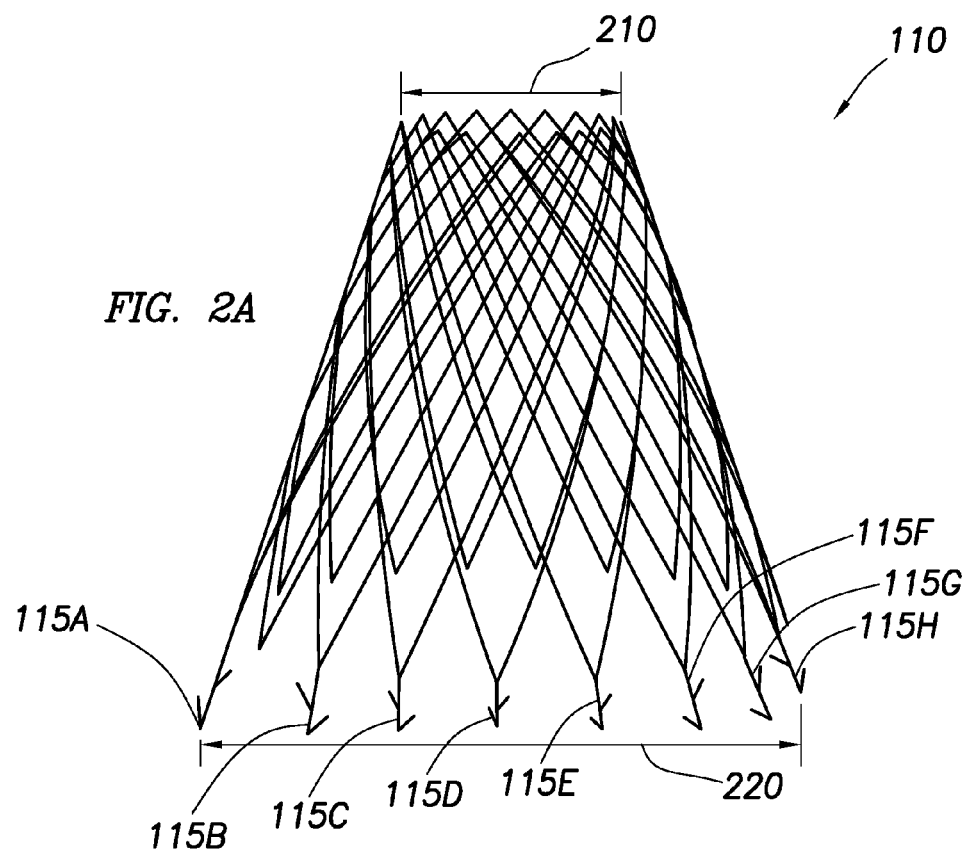
FIGS. 2A-2D illustrate an alternative example embodiment of an implant in accordance with the present disclosure.

FIGS. 2A-2D illustrate an example of implant 110 in accordance with the present disclosure. As shown in FIG. 2A, implant 110 may be made of a metal and cut to form a mesh, a cage, or series of repeating units to allow variations in diameter. For example, implant 110 may include a tubular body of repeating squares, diamonds, hexagons, or any other shape allowing a variation in diameter of implant 110. In first structural configuration as shown in FIG. 2A, implant 110 may have the larger diameter portion initially oriented toward mitral valve 170 (the lower portion with lower diameter 220) and the smaller diameter may be oriented in the left atrium (the upper portion with upper diameter 210). The upper portion may be in free space in the left atrium and have a smaller diameter ready to be expanded in this first structural configuration.

The construction of implant 110 may include a tapered laser cut tube expanded to a predetermined diameter with wall thickness approximately 0.005 inches to approximately 0.050 inches and a strut thickness of approximately 0.010 inches to approximately 0.070 inches and an expanded diameter of approximately 1.00 inch. If the implant is tapered, the large diameter may measure about thirty five millimeters in diameter and the smaller diameter may measure about twenty five millimeters in diameter. In the first structural configuration, the lower portion (i.e. the larger diameter section) may have penetrating members 115 to engage the mitral annulus and hold implant 110 in position during annuls reduction and remain as a permanent implant.

Figure 2B:
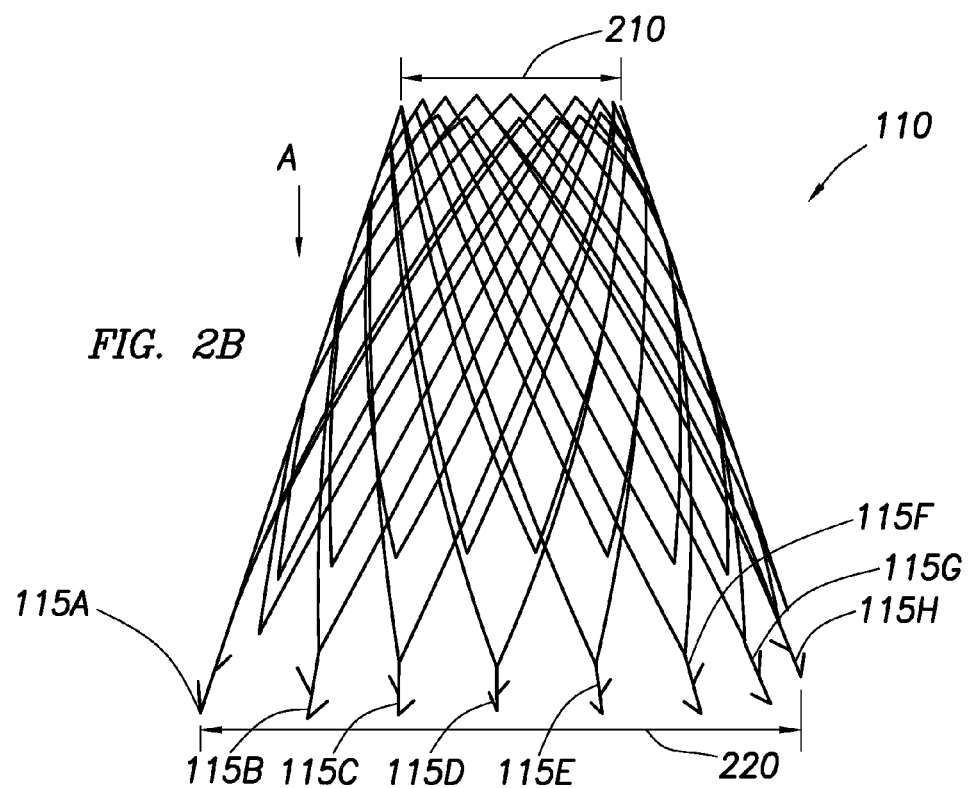

As shown in FIG. 2B, downward force "A" may be applied to implant 110. In some embodiments, piercing members 115A-H may be driven to engage the tissue one at a time. For example, a linear force may drive the hooks or barbs of piercing member 115A into the tissue by pushing at the top of implant 110 above piercing member 115A, thus transmitting a force through to the piercing member 115A, driving it into the tissue. The delivery system or catheter applying the force may then be rotated and actuated again to engage another piercing member 115, for example adjacent piercing member 115B. Once piercing member 115B has been engaged with the tissue, this may be repeated until all piercing members 115 have been engaged with the tissue. Alternatively, in some embodiments, force "A" may be sufficient to engage multiple piercing members 115 at once, rather than engaging only a single piercing member 115 at a time. In some embodiments, all of piercing members 115 may be engaged at once.

Figure 2C:
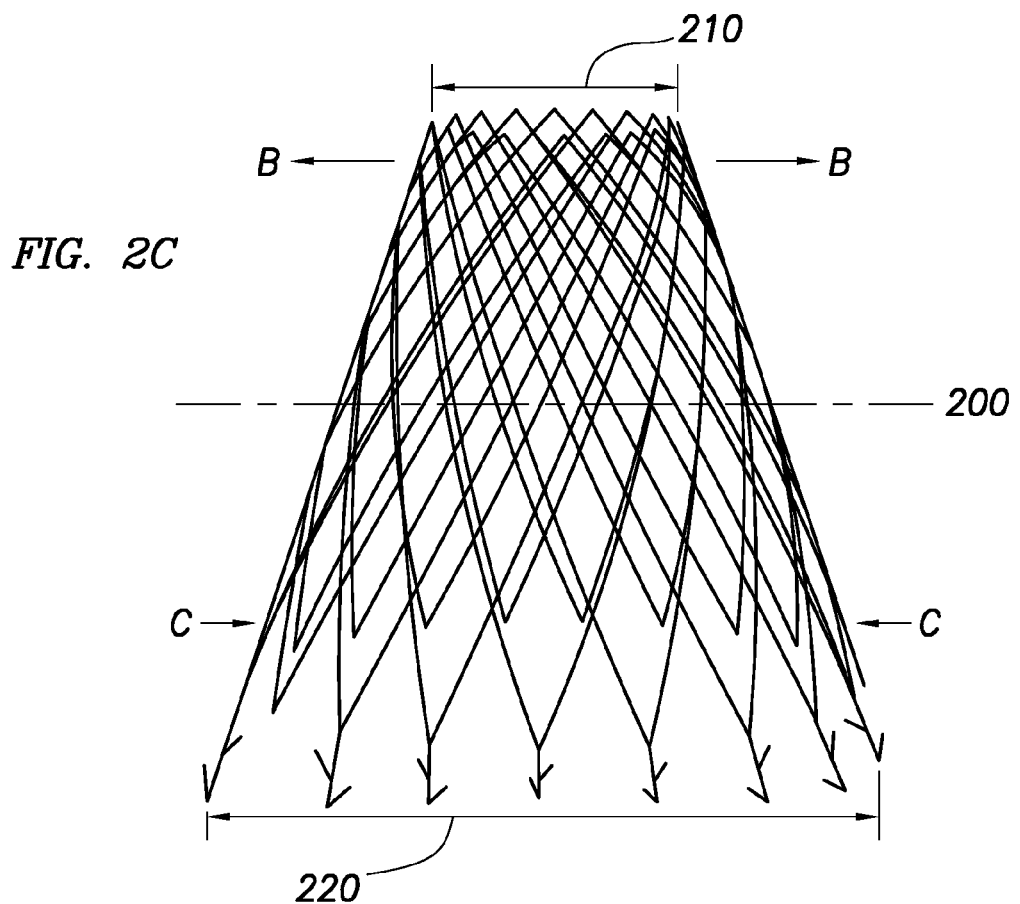
Figure 2D:
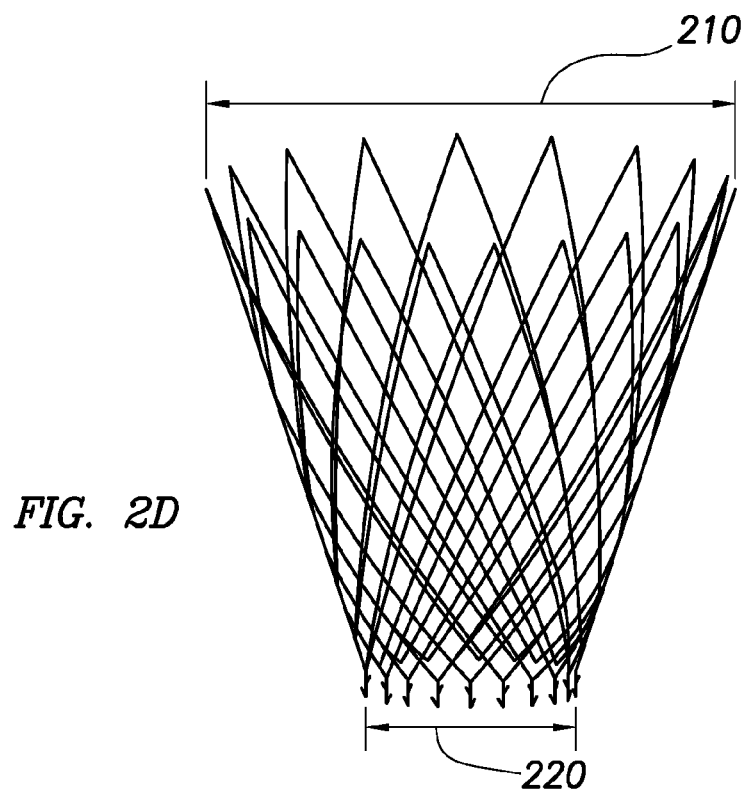

As shown in FIG. 2C, implant 110 may be in a first structural configuration in which upper diameter 210 may be smaller than lower diameter 220. An expansive force "B" may be applied to the upper portion of implant 110. As the expansive force "B" is applied such that the upper diameter 210 is increased, the lower diameter 220 may be decreased due to a reactive reductive force "C" which is generated. A wall of the tubular body of implant 110 may act as a beam in deflection where the upper portion of implant 110, when deflected (e.g. expanded), may cause the lower portion of implant 110 to bend (e.g. contract). This may facilitate the transition from this first structural configuration to a second structural configuration. The lower diameter 220 may be proximate piercing members 115, which are engaged with the mitral valve annulus. Thus, as lower diameter 220 becomes smaller, the diameter of mitral valve 170 becomes smaller. The expansive force "B" may be applied via balloon dilation, mechanical expansion or other means to increase upper diameter 210, thus reducing lower diameter 220. This may effectively invert implant 110's dimensions about axis 200, which may be referred to as an axis of inversion or axis of reflection. In some embodiments, the diameter of implant 110 at axis 200 may remain approximately uniform in a first structural configuration, transitioning between structural configurations, and a second structural configuration. As shown in FIG. 2D, the application of expansive force "B" and thus reactive reducing force "C" may result in implant 110 with upper diameter 210 having a larger length and lower diameter 220 having a shorter length. This may in turn reduce barb-engaged mitral valve 170 to a smaller annulus cross-sectional area, lessening the mitral regurgitation. The structural configuration shown in FIG. 2B may be the second structural configuration of implant 110 in which mitral valve 170 has been reduced in annulus cross-sectional area. Additionally, this second structural configuration may be a final structural configuration that may maintain the size change of mitral valve 170.

Figure 3A:
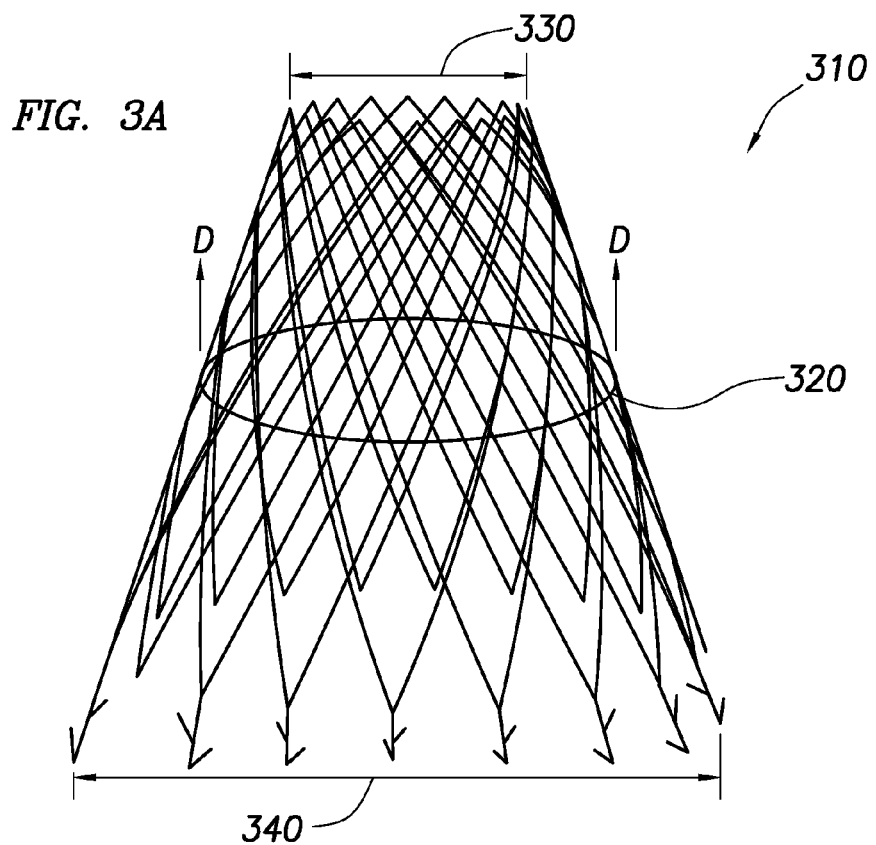
FIGS. 3A-3B illustrate a further alternative example embodiment of an implant in accordance with the present disclosure.
Figure 3B:
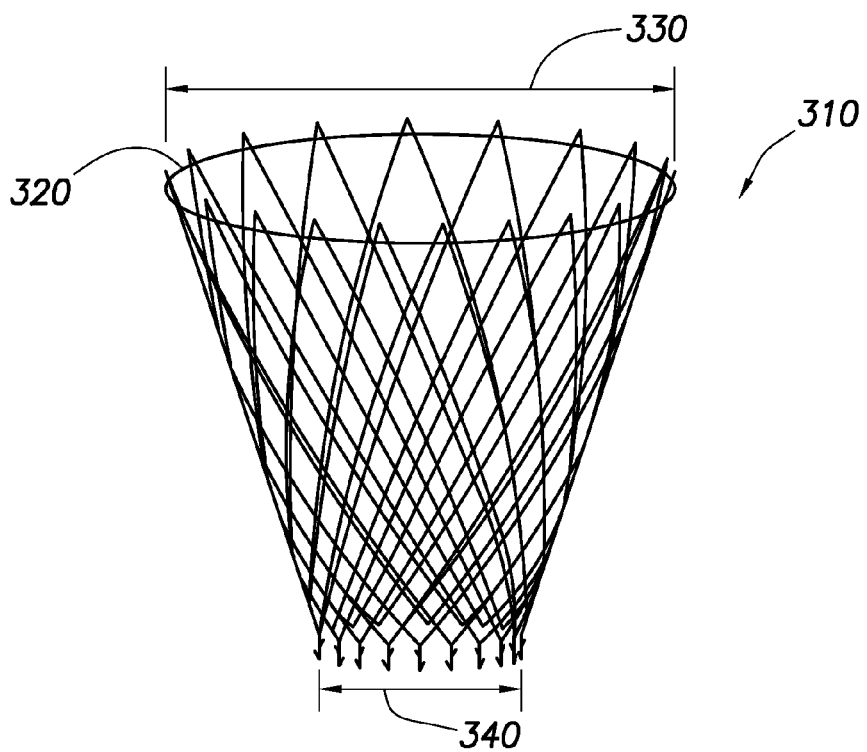

As shown in FIGS. 3A and 3B, an alternative method for applying an expansive force to implant 310 may be the deployment of a ring 320 within implant 310. FIG. 3A illustrates implant 310 in a first structural configuration and FIG. 3B illustrates implant 310 in a second structural configuration. In some embodiments, a fixed ring 320 may be utilized. Fixed ring 320 may be moved vertically to expand the upper portion to increase upper diameter 330, thus causing the lower portion to reduce lower diameter 340 along with the engaged tissue and mitral valve. For example, upward force "D" may be applied to ring 320. However, because of the frustoconical shape of implant 310, the upward force "D" may be translated to an expansive lateral force causing an increase in upper diameter 330. Ring 320 may lock into implant 310 by an interference fit or a mechanical stop built in ring 320 or implant 310, and may maintain implant 310 in the second structural configuration.

Alternatively, an expandable ring 320 may be used rather than a fixed ring. Expandable ring 320 may be positioned within implant 310 and may be delivered and expanded by a catheter using hydraulic or mechanical force to expand ring 320. Ring 320 may be introduced into implant 310's inner diameter where ring 320 may be tilted to allow for manipulation or positioning. Alternatively, ring 320 may be placed at a defined vertical position in implant 310 and ring 320 may be expanded with mechanical or hydraulic force or an extension of the radial dimension. Ring 320 may also serve as a locking mechanism for implant 310 once the second structural configuration or the final position has been reached. The expansion and/or locking of ring 320 may be reversible in nature, thus undoing the expansion of the upper portion. Ring 320 may lock into implant 310 by an interference fit or a mechanical stop built in ring 320 or implant 310.

Figure 4A:
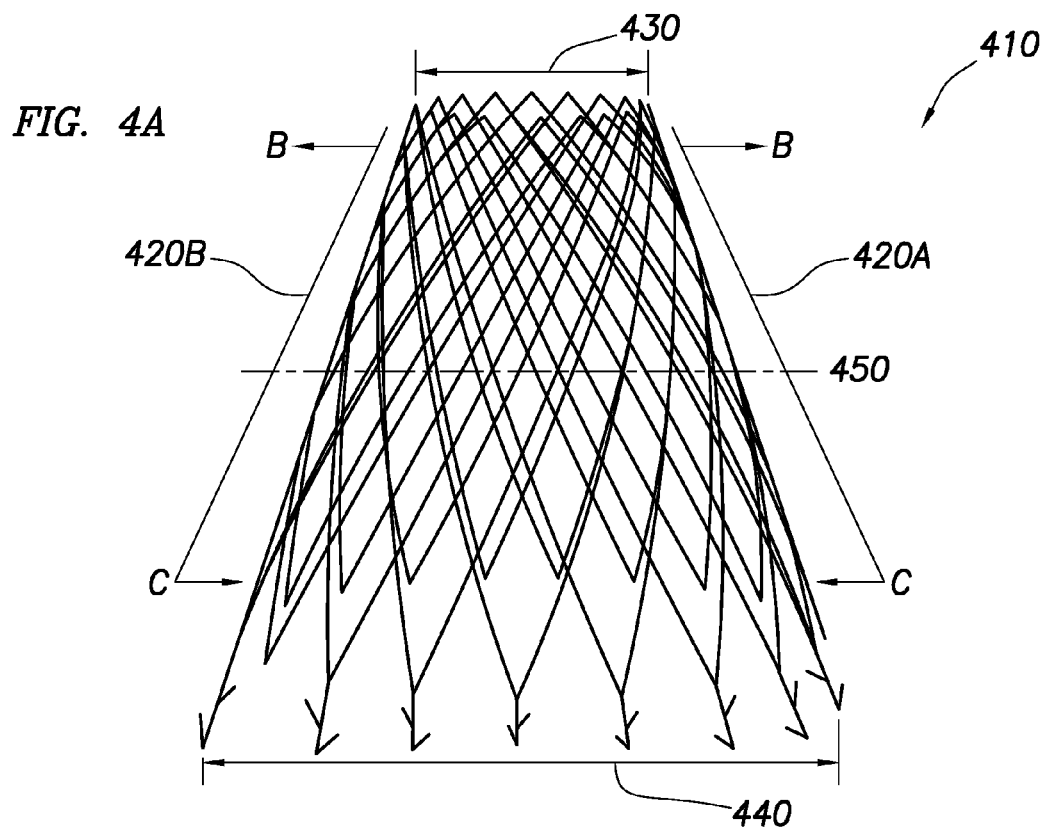
FIGS. 4A-4B illustrate an additional example embodiment of an implant in accordance with the present disclosure.
Figure 4B:
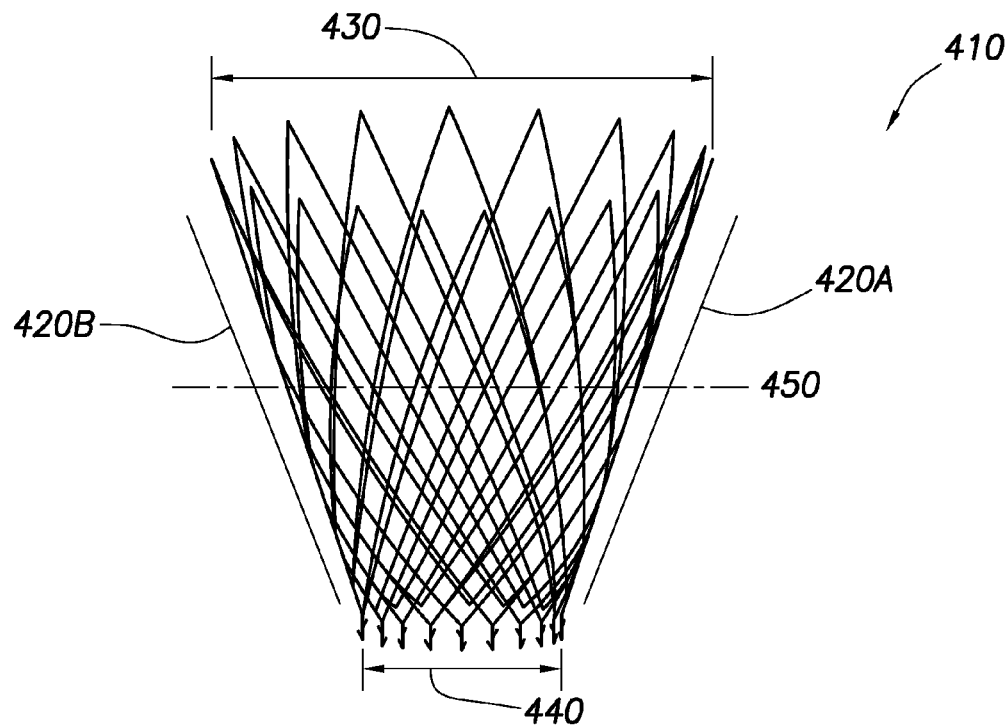

FIGS. 4A and 4B illustrate an additional embodiment of an implant 410 for reshaping mitral valve 170. FIG. 4A illustrates implant 410 in a first structural configuration and FIG. 4B illustrates implant 410 in a second structural configuration. As shown in FIG. 4A, in some embodiments, implant 410 may include one or more support beams 420 (for example, support beams 420A and 420B). Support beams 420 may facilitate the transition of expansive force "B" to the reductive force "C." For example, support beam 420 may operate as a beam in deflection about axis 450. Thus, as expansive force "B" is applied to the upper portion of implant 410, beams 420A and 420B may act as levers with axis 450 as the fulcrum or point of rotation, causing reductive force "C" to reduce lower diameter 440. As expansive force "B" is applied to increase upper diameter 430 and decrease lower diameter 440, implant 410 may transition from a first structural configuration shown in FIG. 4A to a second structural configuration shown in FIG. 4B. As described above, this may reduce the cross-sectional area of mitral valve 170.

Support beams 420A and 420B may be integrally formed with implant 410, for example, as a thicker portion of a wall of the tubular body of implant 410, or a specific alignment of repeating units or elements of the structure of the wall of the tubular body. Alternatively, support beams 420A and 420B may be an additional support component added to implant 410. For example, they may be glued, welded, or otherwise permanently affixed to implant 410.

Figure 5:
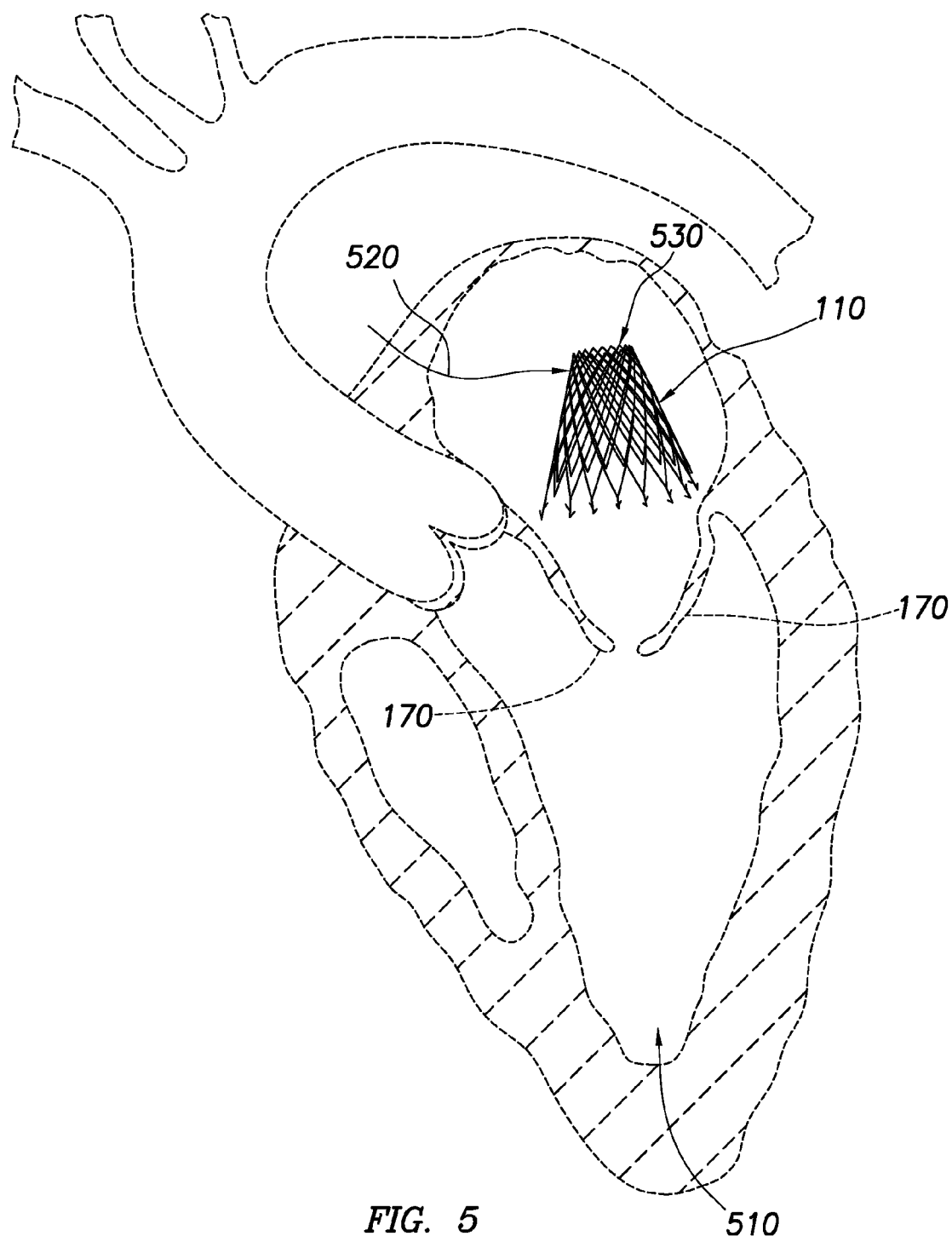
FIG. 5 illustrates examples of delivery routes of an implant, in accordance with the present disclosure.

As shown in FIG. 5, in addition to access to mitral valve 170 through the apex of the heart as shown by 510, access to mitral valve 170 may also be gained via the femoral artery through the aortic valve as shown by 530, or through the venous system and then via trans-septal puncture directly into the left atrium as shown by 520. When accessed via the femoral artery or trans-septally, a delivery catheter may measure about ninety to one hundred and fifty centimeters in length. The end of the catheter may be deflectable via deflection wires creating tension of bias to allow adjustments due to anatomical variations.

Figure 6:
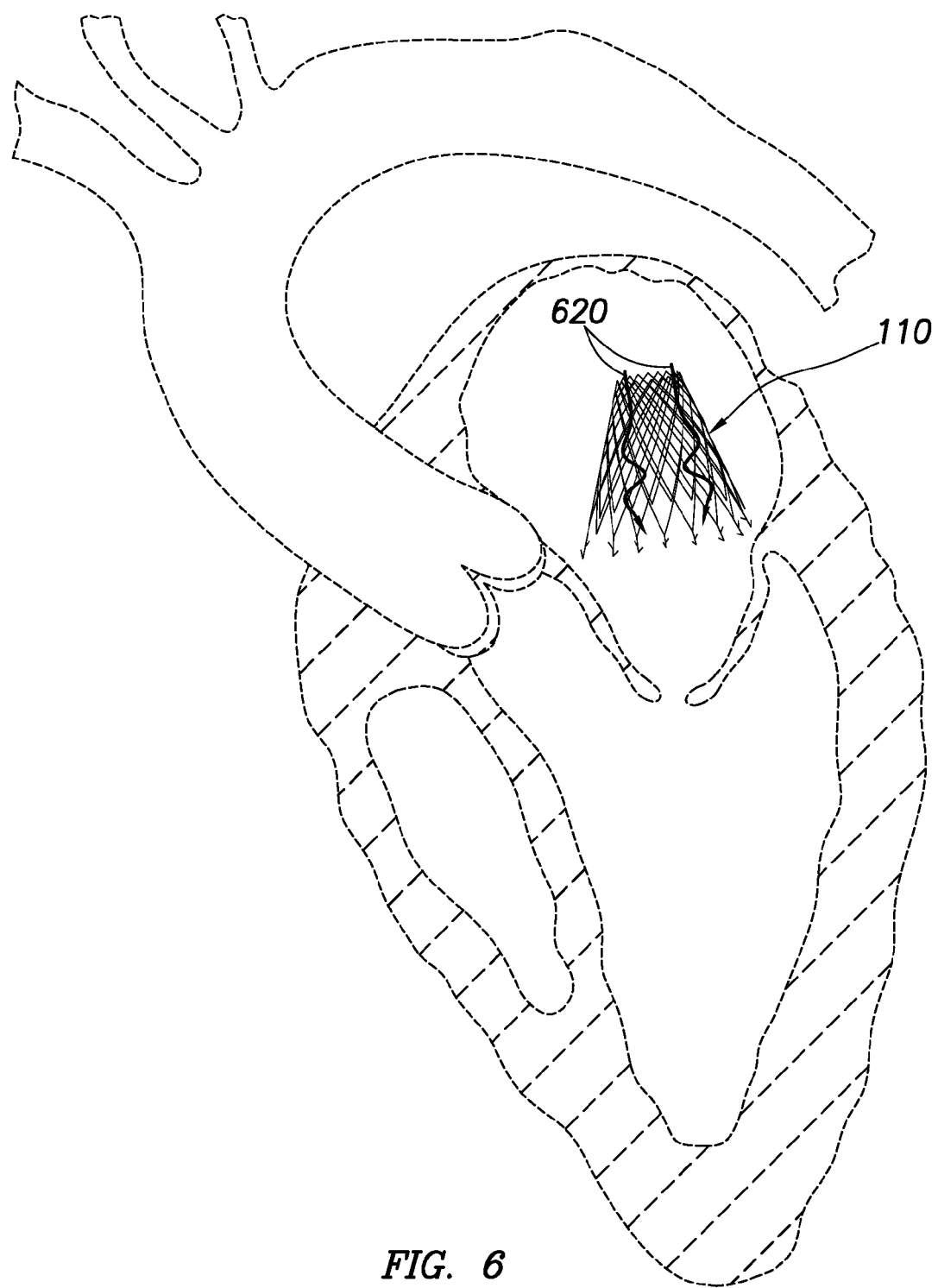
FIG. 6 illustrates an example embodiment of the present disclosure utilizing vibrations, in accordance with the present disclosure.

As shown in FIG. 6, vibration may be applied directly to penetrating members 115 to facilitate the barbs or hooks and/or penetrating members 115 penetrating the tissue. Low frequency vibration, ultrasonic, or Radio Frequency energy may allow a lower insertion force compared to the barb or hook's and/or penetrating members' normal penetration force. Coupling this energy source to implant 110 may allow transmission of small vibrations 620 to the tip of each barb or hook and/or penetrating member 115. Alternatively, each barb or hook and/or penetrating member 115 may have its own independent energy source allowing a variable pattern of frequency or energy around implant 110. Direct tissue contact of the energy element or a coupling to implant 110 may be used but there may be a decrease in efficiency by coupling vibration 620 thereto. The frequency of vibration 620 may be about ten to one hundred Hz (cycles per second) or may be about twenty Hz.

Figure 7:
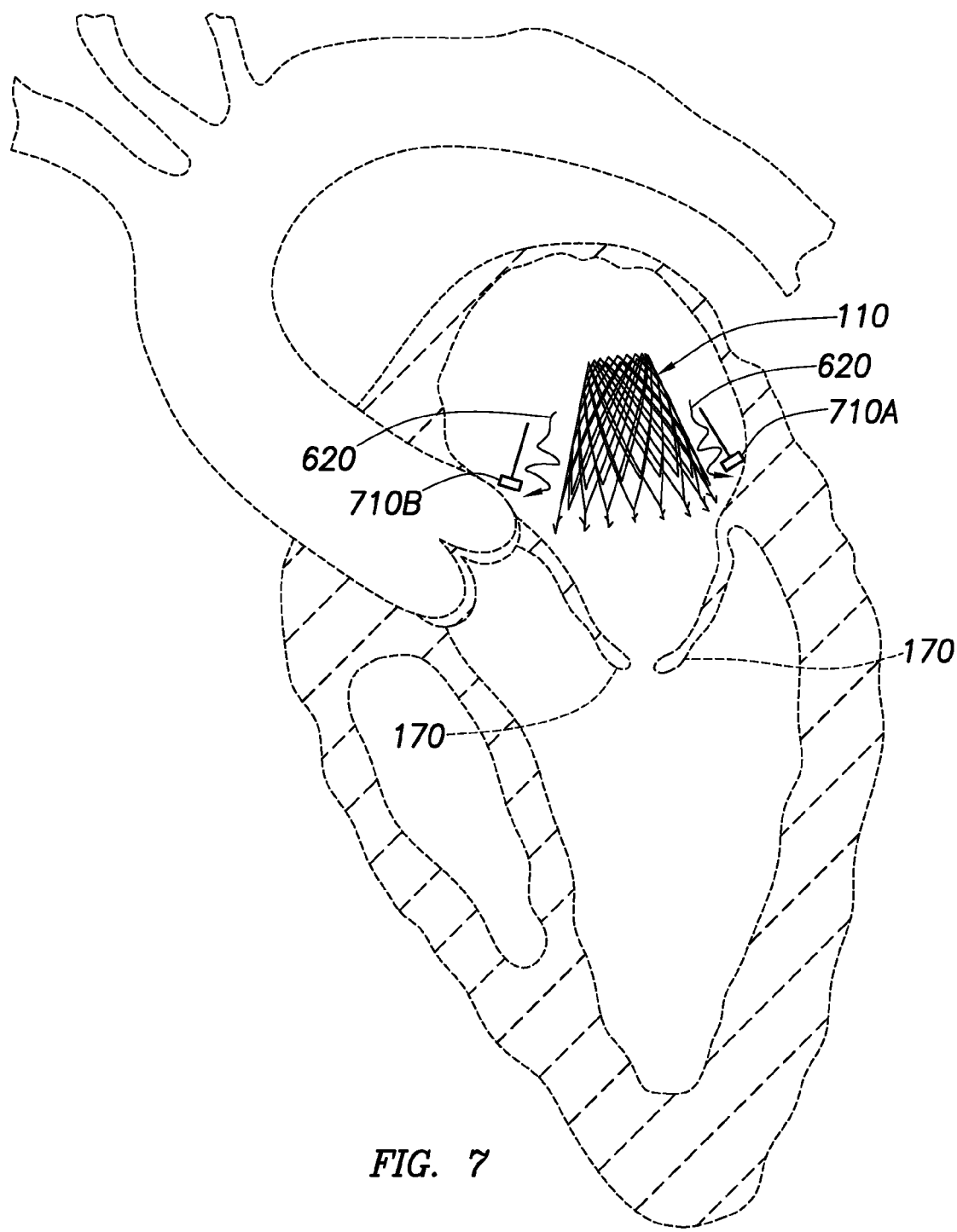
FIG. 7 illustrates an alternative example embodiment of the present disclosure utilizing vibrations, in accordance with the present disclosure.
Figure 8:
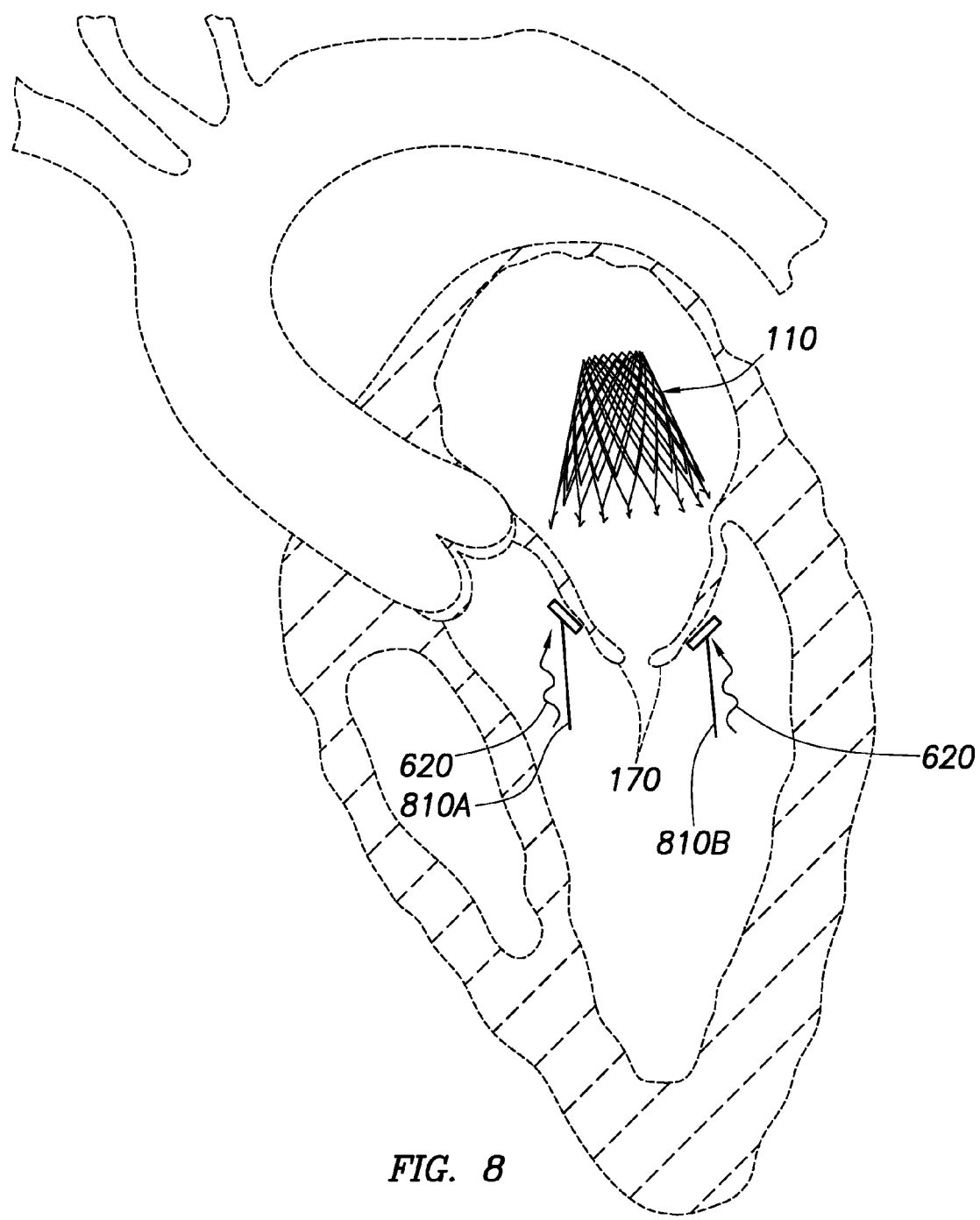
FIG. 8 illustrates an additional example embodiment of the present disclosure utilizing vibrations, in accordance with the present disclosure.

As shown in FIGS. 7 and 8, to aid in the engagement of the penetrating members 115, additional energy may be added to vibrate the tissue surrounding or below mitral valve 170. For example, as shown in FIG. 7, vibration pads 710A and 710B may deliver vibration 620 to the surrounding tissue near the barbs or hooks of penetrating members 115. Pads 710A and 710B may be used to vibrate the tissue near the barb insertion site. Pads 710A and 710B may be completely separate from implant 110 or may be connected to the same delivery system. A separate control for linear and radial motion of pads 710A and 710B may be provided to control the location to provide precise delivery of vibration 620.

As shown in FIG. 8, vibration pads 810A and 810B may also be located below mitral valve 170. This may still provide vibration 620 to facilitate the engagement of barbs or hooks of penetrating members 115 with tissue proximate mitral valve 170. As with the embodiment of FIG. 7, vibration pads 810A and 810B may be completely separate from implant 110 or may be connected to the same delivery system. A separate control for linear and radial motion of pads 810A and 810B may be provided to control the location to provide precise delivery of vibration 620.

Radio frequency (RF) is a rate of oscillation in the range of about three kHz to three hundred GHz, which corresponds to the frequency of radio waves, and the alternating currents, which carry radio signals. RF usually refers to electrical rather than mechanical oscillations. Below is a chart of common nomenclature for different frequency ranges. The range utilized for barb penetration may be somewhere between ELF and HF as the goal is small vibration and not heating of the tissue. Possible user range selection would allow for different tissue types and densities.

TABLE 1

| Frequency | Wavelength | Designation | Abbreviation |
|---|---|---|---|
| 3-30 Hz | $10^5$-$10^4$ km | Extremely low frequency | ELF |
| 30-300 Hz | $10^4$-$10^3$ km | Super low frequency | SLF |
| 300-3000 Hz | $10^3$-100 km | Ultra low frequency | ULF |
| 3-30 kHz | 100-10 km | Very low frequency | VLF |
| 30-300 kHz | 10-1 km | Low frequency | LF |
| 300 kHz-3 MHz | 1 km-100 m | Medium frequency | MF |
| 3-30 MHz | 100-10 m | High frequency | HF |
| 30-300 MHz | 10-1 m | Very high frequency | VHF |
| 300 MHz-3 GHz | 1 m-10 cm | Ultra high frequency | UHF |
| 3-30 GHz | 10-1 cm | Super high frequency | SHF |
| 30-300 GHz | 1 cm-1 mm | Extremely high frequency | EHF |
| 300 GHz-3000 GHz | 1 mm-0.1 mm | Tremendously high frequency | THF |

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. For example, various embodiments may perform all, some, or none of the steps described above. Various embodiments may also perform the functions described in various orders.

Although the present disclosure has been described above in connection with several embodiments; changes, substitutions, variations, alterations, transformations, and modifications may be suggested to one skilled in the art, and it is intended that the present disclosure encompass such changes, substitutions, variations, alterations, transformations, and modifications as fall within the spirit and scope of the appended claims.

What is claimed is:

1. A method comprising:
    inserting an implant proximate a mitral valve, the implant comprising a tubular body and a plurality of piercing members, the tubular body comprising an upper diameter and a lower diameter;
    engaging tissue proximate the mitral valve by the plurality of piercing members on a first side of the mitral valve from within the left atrium;
    coupling at least one of the plurality of piercing members with a location ring that is positioned on a second side of the mitral valve within the left ventricle; and
    transitioning the tubular body from a first structural configuration to a second structural configuration by application of an expansive force to the tubular body proximate the upper diameter, the first structural configuration having the upper diameter smaller than the lower diameter and the second structural configuration having the upper diameter larger than the lower diameter.

2. The method of claim 1, wherein the engaging tissue step further comprises applying vibration to at least one of the plurality of piercing members.

3. The method of claim 1, wherein the engaging tissue step further comprises applying vibration to the tissue proximate the mitral valve either on a same side of the mitral valve as the implant or on a side of the mitral valve opposite the implant.

4. The method of claim 1, wherein the transitioning the tubular body step further comprises applying an upward force on a fixed ring positioned within the tubular body, the fixed ring comprising a diameter larger than the upper diameter in the first structural configuration.

5. The method of claim 1, wherein the transitioning the tubular body further comprises:
    placing an expandable ring proximate the upper diameter; and
    expanding the expandable ring to increase the upper diameter.

6. The method of claim 1, wherein at least one of the plurality of piercing members is covered during the insertion of the implant proximate the mitral valve step.

7. The method of claim 1, wherein at least one of the plurality of piercing members engages the tissue proximate the mitral valve before another of the plurality of piercing members.

* * * * *